US006416549B1

(12) United States Patent
Chinn et al.

(10) Patent No.: US 6,416,549 B1
(45) Date of Patent: Jul. 9, 2002

(54) ANTITHROMBOGENIC ANNULOPLASTY RING HAVING A BIODEGRADABLE INSERT

(75) Inventors: Joseph A. Chinn; R. Michael Casanova, both of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/357,666

(22) Filed: Jul. 20, 1999

Related U.S. Application Data

(63) Continuation-in-part of application No. 09/356,921, filed on Jul. 19, 1999, now abandoned.

(51) Int. Cl.[7] ................................................. A61F 2/24
(52) U.S. Cl. ........................................................ 623/2.36
(58) Field of Search ............................. 623/2.36, 1.42, 623/1.43, 901, 2.38, 2.41

(56) References Cited

U.S. PATENT DOCUMENTS

| | | | |
|---|---|---|---|
| 3,511,684 A | 5/1970 | Huffaker | 117/47 |
| 3,585,647 A | 6/1971 | Gajewski et al. | 3/1 |
| 3,616,935 A | 11/1971 | Love et al. | 210/500 |
| 3,634,123 A | 1/1972 | Eriksson et al. | 117/47 |
| 3,755,218 A | 8/1973 | Yen et al. | 260/9 |
| 3,896,813 A | 7/1975 | Kurtz | 128/335.5 |
| 3,987,797 A | 10/1976 | Stephenson | 128/335.5 |
| 4,055,861 A | * 11/1977 | Carpentier et al. | 623/2.36 |
| 4,107,121 A | 8/1978 | Stoy | 260/29.6 |
| 4,116,898 A | 9/1978 | Dudley et al. | 260/17 |
| 4,118,485 A | 10/1978 | Eriksson et al. | 424/183 |
| 4,254,180 A | 3/1981 | Kline | 428/323 |
| 4,265,927 A | 5/1981 | Eriksson et al. | 427/2 |
| 4,291,133 A | 9/1981 | Horak et al. | 525/74 |
| 4,302,368 A | 11/1981 | Dudley et al. | 260/17.4 |
| 4,326,532 A | 4/1982 | Hammar | 128/349 |
| 4,331,697 A | 5/1982 | Kude et al. | 427/2 |

(List continued on next page.)

OTHER PUBLICATIONS

US 5,556,632, 09/1996, Kohler et al. (withdrawn)
Chacques, J. C., et al., Absorbable Ring for Pediatric Valvuplasty,Supplement IV Circulation vol. 82, No. 5, Nov. 1990, pp 82–88.
Olanoff, L. S., et al., Sustained Release of Gentamicin From Prosthetic Heart Valves, American Society for Artificial Internal Organs vol. XXV, 1979, pp 334–338.
Burkoth, A., et al., A New Class of Hotopolymerizable Surface Eroding Polymers for Medical Applications,Surfaces in Biomaterials Foundation, 1997, pp 58–63.
Solomon, D. D., et al., Antibiotic Releasing Polymers, Journal of Controlled Release, 6 (1987), pp 343–352.
Mee, R. B. B., et al., Congenital Heart Surgery, Current Science, 1992, pp 249–258.
Chachques, J. C., et al., Current Status of Valvularsurgery, Current Opinion in Cardiology, 1994, 9:186–190.

(List continued on next page.)

Primary Examiner—David H. Willse
Assistant Examiner—Choon Koh
(74) Attorney, Agent, or Firm—Blossom E. Loo; Timothy L. Scott

(57) ABSTRACT

This invention provides an antithrombogenic annuloplasty rings, and methods for making the same, wherein the annuloplasty rings have a desired degree of initial rigidity to facilitate ease of handling during implantation but which becomes flexible some time after implantation. The annuloplasty ring contains a relatively rigid insert enclosed by a fabric sheath, the insert being at least partly comprised of a biodegradable material. Following surgical implantation of the annuloplasty ring, the rigid insert component of the ring, upon exposure to blood and/or other physiological fluids, undergoes a controlled biodegradation which decreases its rigidity, thereby increasing the flexibility of the implanted annuloplasty ring. Furthermore, at least some portion of the annuloplasty ring has incorporated into or onto its structure one or more antithrombogenic agents or materials in a manner which reduces the likelihood of thrombosis following implantation.

25 Claims, 1 Drawing Sheet

U.S. PATENT DOCUMENTS

| | | | |
|---|---|---|---|
| 4,442,133 A | 4/1984 | Greco et al. | 427/2 |
| 4,521,564 A | 6/1985 | Solomon et al. | 525/54.1 |
| 4,526,714 A | 7/1985 | Feijen et al. | 260/112 |
| 4,542,169 A | 9/1985 | Costerton | 523/121 |
| 4,581,028 A | 4/1986 | Fox, Jr. et al. | 623/2 |
| 4,592,920 A | 6/1986 | Murtfeldt | 427/2 |
| 4,600,652 A | 7/1986 | Solomon et al. | 428/423.3 |
| 4,612,337 A | 9/1986 | Fox, Jr. et al. | 523/113 |
| 4,634,762 A | 1/1987 | Feijen et al. | 530/350 |
| 4,642,242 A | 2/1987 | Solomon et al. | 427/2 |
| 4,676,974 A | 6/1987 | Hofmann et al. | 424/9 |
| 4,678,660 A | 7/1987 | McGary et al. | 424/25 |
| 4,678,671 A | 7/1987 | Feijen et al. | 424/443 |
| 4,713,402 A | 12/1987 | Solomon | 523/112 |
| 4,749,585 A | 6/1988 | Greco et al. | 427/2 |
| 4,895,566 A | 1/1990 | Lee | 604/266 |
| 4,917,686 A | 4/1990 | Bayston et al. | 604/265 |
| 4,952,149 A | 8/1990 | De Leon et al. | 427/2 |
| 4,952,419 A | 8/1990 | De Leon et al. | 427/2 |
| 4,973,493 A | 11/1990 | Guire | 427/2 |
| 4,979,959 A | 12/1990 | Guire | 623/66 |
| 5,013,306 A | 5/1991 | Solomon et al. | 604/265 |
| 5,053,453 A | 10/1991 | Ku | 525/54.1 |
| 5,103,306 A | 4/1992 | Weiman et al. | 358/133 |
| 5,104,407 A | 4/1992 | Lam et al. | 623/2 |
| 5,217,493 A | 6/1993 | Raad et al. | 623/11 |
| 5,263,992 A | 11/1993 | Guire | 623/66 |
| 5,308,641 A | 5/1994 | Cahalan et al. | 427/2 |
| 5,414,075 A | 5/1995 | Swan et al. | 568/333 |
| 5,492,763 A | 2/1996 | Barry et al. | 428/457 |
| 5,512,329 A | 4/1996 | Guire et al. | 427/508 |
| 5,624,704 A | 4/1997 | Darouiche et al. | 427/2.24 |
| 5,679,659 A | 10/1997 | Verhoeven et al. | 514/56 |
| 5,688,516 A | 11/1997 | Raad et al. | 424/409 |
| 5,716,397 A | 2/1998 | Myers | 623/2 |
| 5,741,551 A | 4/1998 | Guire et al. | 427/407.1 |
| 5,865,814 A | 2/1999 | Tuch | 604/265 |
| 5,877,263 A | 3/1999 | Patnaik et al. | 525/453 |

OTHER PUBLICATIONS

Raad, I., Effect of Anti–Infective Coatings on Biofilms, Surfaces in Biomaterials Foundation 1996, pp. 5–8.

Sherertz, R. J., et al., Efficacy of Dicloxacillin–Coated Polyurethane Catheters in Preventing Subcutaneous Staphylococcus Areus Infection in Mice, Antimicrobial Agents and Chemotherapy, Aug. 1989, pp 1174–1178.

Hirudin Immobilization to Produce Antithrombic Surfaces, Cardiovascular Science and Technology: Basic and Applied Dec. 1–3, 1990.

Anderson, A. B., et al., Photochemical Immobilization of Heparin to Reduce Thrombogenesis, 20th Annual Meeting of the Society for Biomaterials, Apr. 5–9, 1994, p 75.

Chachques, J. C., et al., Study of Muscular and Ventricular Function in Dynamic Cardiomyoplasty: A Ten–Year Follow Up, The Journal of Heart and Lung Transplantation, vol. 16, No. 8, pp. 854–868.

* cited by examiner

ANTITHROMBOGENIC ANNULOPLASTY RING HAVING A BIODEGRADABLE INSERT

This application is a continuation-in-part of U.S. patent application Ser. No. 09/356,921, filed Jul. 19, 1999, now abandoned.

FIELD OF THE INVENTION

This invention relates generally to devices for use in the surgical repair of heart pathologies, and, more particularly, to antithrombogenic annuloplasty rings which contain relatively rigid biodegradable inserts.

DESCRIPTION OF THE RELATED ART

Human heart valves can become deformed or otherwise damaged by any of a number of processes brought on by normal aging and/or disease pathologies. For example, degenerative diseases can cause the valve annulus to become enlarged to the point where the leaflets attached to it cannot fully close. This situation, known as valve incompetence, eventually requires surgical correction by valve repair or replacement procedures. Of the surgical options available for valve reconstruction, valvular annuloplasty represents the procedure most frequently performed, particularly for the tricuspid and mitral valves. Valvular annuloplasty is an operation whereby ring-shaped devices or bands, known as annuloplasty rings, are sewn to the distended valve annulus in order to restore it to its normal, undilated circumference.

Annuloplasty rings are most typically either highly flexible or are stiff and comparatively rigid. Rigid rings typically consists of an open wire element completely covered with cloth. The wire is somewhat stiff yet resiliently deformable and is not intended to be removable from the cloth covering. These annuloplasty rings, because of their rigidity, lie flat and maintain their somewhat oval shape during implantation. Although a rigid ring's oval shape has been claimed to enhance the competence of the repaired valve, its rigidity can also impede the beneficial flexing movements of the native annulus during the cardiac cycle. Flexible annuloplasty rings generally consist of a soft core of elastomeric material, e.g., silicone rubber, completely enclosed by a sheath of biocompatible cloth. Because of their flexibility, these rings can be difficult to handle during surgical manipulations and generally must be supported during implantation by a holder which is subsequently removed before tying off the implanting sutures.

To overcome some of the deficiencies of flexible and rigid ring structures, an annuloplasty ring would desirably be stiff during handling and implantation, but then become flexible after implantation. As disclosed in U.S. Pat. No. 5,716,397, an annuloplasty ring may consist of a flexible ring into which a rigid structure is inserted to provide temporary rigidity during implantation. Once the ring is implanted and tested, the rigid structure may be removed. However, this approach requires undesirable additional handling after the ring is implanted. Another annuloplasty ring, as disclosed in U.S. Pat. No. 5,104,407, consists of a ring constructed partially of a flexible material and partially of a rigid material. Unfortunately, this ring will be difficult and costly to manufacture and will suffer from the drawbacks afflicting both flexible and rigid rings. In an alternative approach, Chachques et al. (Circulation 82(5), Supplement IV, 82–88, 1990) describes absorbable prosthetic rings for use in pediactric valvular annuloplasty. The rings are reported to address concerns over secondary valvular stenosis in children that can result from implantation of known annuloplasty rings. The rings described by Chachques et al. are synthesized from biodegradable polydioxanone and covered with a porous extensible sewing sheath to allow contact between the polydioxanone, the blood and the endocardium. As a result of this contact, the polydioxanone ring is reported to undergo degradation following implantation.

Many complications associated with the use of implantable medical devices stem from the complex cellular and humoral reactions which occur when a foreign material comes into contact with blood and/or other physiological fluids. Among the most significant of these are the rapid thrombogenic actions which can occur following implantation of a medical device. Initial contact of a device with blood results in deposition of plasma proteins, such as albumin, fibrinogen, immunoglobulin, coagulation factors, and complement proteins. The cellular activities which follow can, among other things, lead to vascular constriction which can hinder blood flow, thrombosis and thrombus accumulation that can result in thromboembolism and stroke, and inflammatory reactions which can damage or impair the function of a medical device.

A variety of methods and compositions have been reported for increasing the thromboresistance of medical device surfaces by bonding or incorporating into or onto the device one or more antithrombogenic agents, such as heparin, hirudin, albumin, phospholipids, streptokinase, tissue plasminogen activator (TPA) or urokinase, hydrophilic polymers such as hyaluronic acid, chitosan, methyl cellulose, and poly(ethylene oxide), poly(vinyl pyrrolidone), growth factors such as endothelial cell growth factor, epithelial growth factor, osteoblast growth factor, fibroblast growth factor, platelet derived growth factor (PDGF), and angiogenic growth factor, and other proteins, carbohydrates and fatty acids.

The present invention is directed to providing annuloplasty rings having antithrombogenic properties which overcome, or at least reducing the effects of, one or more of the problems set forth above.

SUMMARY OF THE INVENTION

This invention provides an antithrombogenic annuloplasty ring having sufficient initial rigidity, i.e., prior to implantation, to facilitate ease of handling during surgical manipulations, but which becomes flexible to a desired extent following implantation. The foregoing is accomplished by use of a relatively rigid biodegradable annuloplasty ring insert as a component of an annuloplasty ring. Upon implantation of an annuloplasty ring containing a biodegradable ring insert of this invention, the insert undergoes degradation in the patient's body as a result of its contact with blood and/or other physiological fluids. The degradation of the biodegradable insert causes a decreasing degree of rigidity of the annuloplasty ring as the insert material is degraded and/or resorbed by the patient's body.

Therefore, in one aspect of the present invention, there is provided an annuloplasty ring which comprises a biodegradable ring insert and a fabric sheath enclosing the ring insert, wherein the fabric sheath and/or the biodegradable insert have undergone one or more antithrombogenic treatment processes. The ring insert of the annuloplasty ring is at least partly comprised of a biodegradable material selected from any of a variety of biodegradable polymers, including polyanhydrides, polyglycolides, polylactides, polyorthoesters, and other like materials. In one illustrative embodiment, the biodegradable insert is comprised of a highly cross-linked polyanhydride material, particularly one that is photopolymerizable, such as that produced by the photopolymerization of methacrylate anhydride monomers. The fabric sheath which encloses the biodegradable insert, or the biodegradable insert itself, are preferably treated either before, after, or simultaneous with the fabrication of the annuloplasty ring in a manner which causes the incorporation of one or more antithrombogenic agents into or onto the device. The biodegradable insert may further comprise, in addition to the biodegradable materials mentioned above, one or more other components, e.g., plasticizers, stabilizers, pigments, dyes, radio-opaque materials, lubricants, antioxidants, bioactive agents, antimicrobial agents, and the like, depending on the requirements and/or preferences for a particular implementation.

In a further aspect of the invention, there is provided a method for making an antithrombogenic annuloplasty ring by forming a biodegradable ring insert at least partly comprised of a material selected, for example, polyanhydrides, polyglycolides, polylactides, and polyorthoesters enclosing the ring insert within a fabric sheath. The ring insert may be formed as a solid part, may be comprised of fibrous materials, or some combination thereof, and is fabricated by any of a variety conventional techniques available for forming shaped articles from polymeric materials, including, without limitation, extrusion, molding, machining, casting, spinning, and other like processes. At some point during fabrication and/or assembly of the annuloplasty ring, or after assembly but prior to implantation, at least some portion of the ring insert and/or the fabric sheath, or some other component of the annuloplasty ring, is treated with an antithrombogenic treatment process in order to cause the incorporation of at least some antithrombogenic agent into or onto a desired portion or portions of the annuloplasty ring.

BRIEF DESCRIPTION OF THE DRAWINGS

The invention may be understood by reference to the following description taken in conjunction with the accompanying drawings, in which like reference numerals identify like elements, and in which.

Figure 1A:
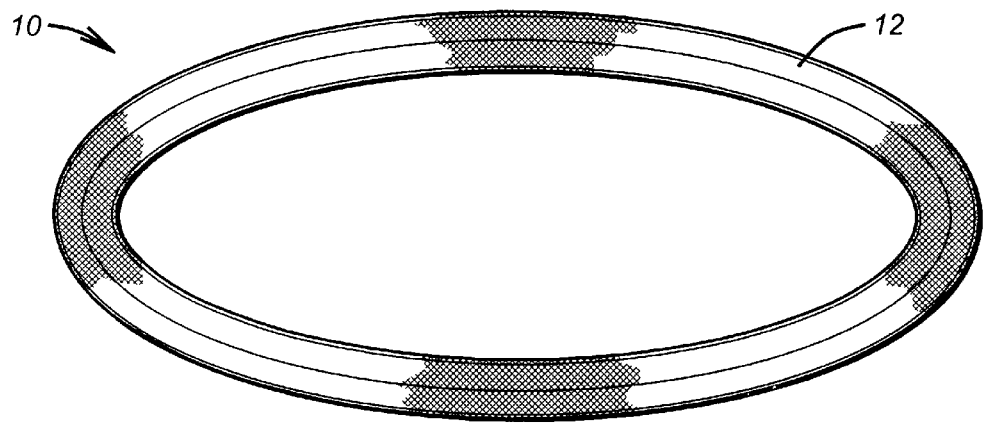
FIG. 1A illustrates one embodiment of the present invention in which the annuloplasty ring is a complete ring.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claim.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1B:
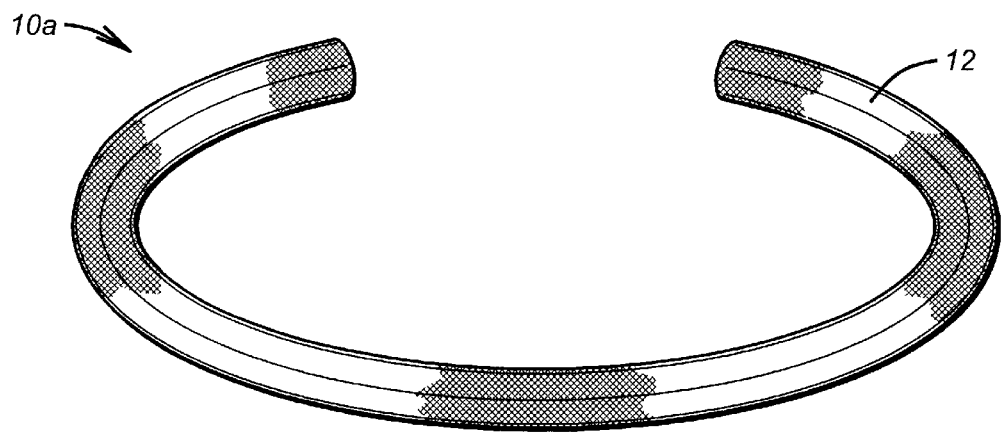
FIG. 1B illustrates one embodiment of the present invention in which the annuloplasty ring is an incomplete ring.
Figure 2:
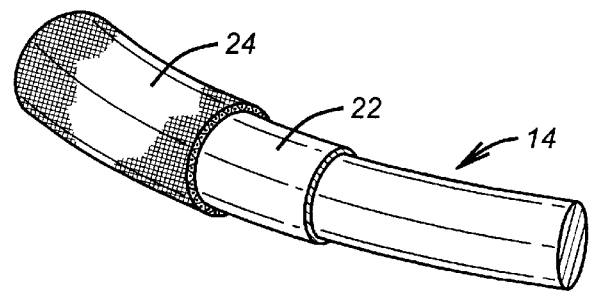
FIG. 2 illustrates a partial section of an annuloplasty ring according to one embodiment of the present invention, showing the positional relationship between the biodegradable ring insert, the covering material, and the outer fabric sheath.

FIGS. 1A and 1B depict two illustrative annoloplasty rings, 10 and 10a, respectively, according to the present invention. The annuloplasty rings each comprise a biodegradable ring insert (not shown) and a sheath 12 enclosing the biodegradable insert, the sheath 12 being constructed of a biocompatible material. The annuloplasty ring 10 of FIG. 1A represents a complete, i.e., closed, annuloplasty ring, whereas the annuloplasty ring 10 of FIG. 1B represents an incompete ring. In FIG. 2, a partial section of an annuloplasty ring is shown in order to illustrate the biodegradable ring insert 14 enclosed within the fabric sheath 24. FIG. 2 further depicts an elastomeric-like covering material 22 positioned between the ring insert 14 and the fabric sheath 24, which may be desired for certain embodiments. As described herein, the fabric sheath 24, elastomeric-like covering material 22 and/or the ring insert 14 will have incorporated therein or thereon one or more antithrombogenic agents to improve in vivo compatibility of the device.

The biodegradable annuloplasty ring insert of the present invention is generally comprised of one or more materials capable of being formed into a desired ring shaped article which has a sufficent degree of rigidity and which degrades with acceptable kinetics upon exposure to the physiological environment into which an annuloplasty ring is implanted. Examples of materials suitable for use in forming a biodegradable insert according to this invention may include, without limitation, polyanhydrides, polylactides, polyglycolides, dextran, hydroxyethyl starch, gelatin, derivatives of gelatin, polyvinylpyrolidone, polyvinyl alcohol, poly-N-(2-hydroxypropyl)methacrylamide, polyglycols, polyesters, poly(orthoesters), poly (esteramides) and other like materials.

In one preferred aspect of the present invention, the material used to form the biodegradable insert is selected from "surface eroding" polymers, e.g., those which undergo a controlled degradation primarily along the surface of the insert, rather than a material which undergoes bulk degradation and is more subject to fragmentation. Such materials are generally characterized by a substantially microscopic degradation, rather than one which results in the generation of macroscopic particulate matter. By employing surface eroding polymers in the fabrication of the ring insert, there is a reduced possibility of embolic complications associated with the release of fragments of the insert material during degradation. Such fragments may become lodged in the fabric sheath which surrounds the insert, possibly leading to an undesirable inflammatory response, or may make their way into the blood stream of the patient, possibly leading to a stroke. Surface eroding polymers suitable for use in forming a biodegradable ring insert according to this invention may include, for example, polyanhydrides and polyorthoesters.

One particularly illustrative surface eroding polymer that may be used for forming a biodegradable ring insert is a polyanhydride. A cross-linked polyanhydride material may be produced using essentially any synthetic approach available to the skilled individual. In one example, a polyanhydride material may be produced from photopolymerizable methacrylate anhydride monomers. Dimethacrylated anhydride monomers may be synthesized, for example, from precursor diacid molecules of sebacid acid or 1,6-bis(p-carboxyphenoxy)-hexane, as described in Anseth et al. (Surfaces in Biomaterials, 1997 Symposium Notebook, pgs. 58–62). The resulting monomers may be polymerized into homopolymers or copolymers by dissolving a suitable photoinitiator, such as 2,2-dimethoxy-2-phenylacetophenone (DMPA, Ciba Geigy) or camphorquinone (CQ, Aldrich) and ethyld-4-N,N-dimethylaminobenzoate (4EDMAB, Aldrich), in the monomer at a concentration typically ranging from about 0.01 wt.% to about 10 wt.%. Polymerization may be initiated with ultraviolet light, visible light, or with another suitable energy source, at an intensity and for a duration effective to produce the desired polymeric material. Other photopolymerizable anhydride monomers, and their methods of synthesis and polymerization into cross-linked polyanhydride networks are known and will also be apparent to the skilled individual in view of this disclosure.

The biodegradable materials used for fabricating an annuloplasty ring insert according to this invention will advantageously exhibit controllable biodegradability, bioresorbability, and/or overall biocompatibility within living tissue. Of course, it is preferred that the biodegradable insert material is substantially biocompatible, such that both the insert material and the products resulting from its degradation are physiologically benign, e.g., are not overly toxic to the point of compromising the outcome of the annuloplasty procedure or the health of the patient. The biodegradation of these materials will preferably result in degradation products having a physiologically neutral pH, or having a pH sufficiently near to physiological neutrality that the products do not induce any pH-related disturbances in or around the tissue into which the annuloplasty ring is implanted. It should be recognized that variations in the degradation rate of the ring insert may depend not only on the characteristics of the insert composition, but also on the overall health of the patient, variations in anticipated immune reactions of the patient to the implant, the site of implantation, and other clinical indicia apparent to the skilled individual.

The degradation kinetics and mechanical properties of the biodegradable insert may be independently controlled. For example, the skilled individual will recognize that the initial rigidity of the biodegradable insert may vary somewhat depending on the composition of the insert, but that this parameter is nonetheless controllable through the manipulation of synthesis, cross-linking, and/or other processing conditions, to provide the insert with a desired rigidity. By controlling the cross-linking density of a polyanhydride material, e.g., by varying the molecular weight between the double bonds, the mechanical properties of the resulting cross-linked polyanhydride material can be altered from being quite flexible to highly rigid. Moreover, by changing the hydrophobicity of the monomer molecules or comonomer mixture that is reacted, the degradation time scale of the final polymer network may be controlled. For example, a significant increase in the degradation rate occurs as the amount sebacic acid is increased in copolymers produced from sebacid acid and 1,6-bis(p-carboxyphenoxy)-hexane. Polyanhydride homopolymers comprised of cross-linked sebacid acid degrade within a matter of days, while homopolymers of 1,6-bis(p-carboxyphenoxy)-hexane degrade in approximately one year (Anseth, 1997). Thus, by copolymerizing sebacic acid and 1,6-bis(p-carboxyphenoxy)-hexane at various ratios, copolymers can be provided with desired degradation kinetics.

The method of making the biodegradable insert is not specifically restricted, and is limited only by the techniques available in the art for forming shaped articles from polymeric materials. The ring insert may be comprised or a solid article, may be a fibrous article constructed, for example, of cabled fibers, woven or non-woven fabric, or may be a combination of solid and fibrous materials. Typically, the devices are composed of substantially solid articles which are fabricated from the biodegradable materials described herein using conventional polymer processing techniques such as injection molding, gel or melt extrusion, machining, and the like. A ring insert containing some fibrous component may be fabricated using conventional fiber-forming techniques such as melt spinning, gel spinning, solution spinning, dry spinning, etc. Such processing techniques and procedures are well known in the art and will not be described herein in further detail.

Preferably, the biodegradable insert will be fabricated using conventional molding techniques, wherein polymerization and/or cross-linking occur either in the mold or just prior to filling the mold, depending on the properties and characteristics of the material being used. In one illustrative process, monomer molecules are provided in an appropriate medium within a mold having the desired ring or partial ring geometry and a suitable stimulus is applied to effect polymerization and/or cross-linking within the mold. For example, when using the metharcrylated anhydride monomers described above, polymerization may be effected in the presence of a photoinitiator by exposure of the mold to an appropriate light source, generally in the ultraviolet or visible spectrum, at an intensity and for a duration effective to result in the desired degree of polymerization and/or cross-linking of the material within the mold. Of course, in this situation, the mold will be one that is comprised of a material that is sufficiently transparent to the light energy necessary to effect polymerization.

As is known in the art, the shape of the biodegradable insert will generally be that of an oval or annular shaped partial or complete ring, although other shapes could be tailored, as desired, for the unique requirements of a given implementation. A partial, incomplete ring, i.e., one having a shape similar to the letter "C", as illustrated in FIG 1B, may be preferred over the completely closed ring illustrated in FIG. 1A in that it allows for a somewhat improved degree of manipulation during surgical implantation.

In addition to the biodegradable insert described above, the annuloplasty ring of this invention will generally further comprise an extensible fabric sheath surrounding the biodegradable insert. The use of a cloth or fabric mesh to enclose various plastic and/or metal members which are subsequently surgically implanted in the human body is known. Such polymeric sheaths are typically comprised of a fabric or fabric-like polymeric material having a relatively high porosity. For example, the sheath may be a fabric material made from polyethyleneterephthalate, polytetrafluoroethylene, polyester (polyacetate), polyethylene, or other such materials known in the art. During implantation, the sheath serves to facilitate surgical fixation of the annuloplasty ring by the surgeon. In addition, during biodegradation of the insert in the patient, the fabric sheath may advantageously participate in the fibroblastic reaction occurring at the site of implantation involving interstitial fibroblast proliferation as well as production of elastin and collagen fibers.

It is generally preferred that the porosity of the fabric sheath is sufficiently high to allow an adequate flow of physiological fluids and other materials necessary to stimulate degradation of the biodegradable insert. However, the porosity of the sheath should not be so high that unacceptably large fragments of biological insert may reach the bloodstream if such fragments are released during degradation of the insert. In this regard, one important advantage of using a surface eroding biodegradable polymer described herein for the production of a ring insert is that these materials do not release undesirably large particulate fragments during degradation. Consequently, there is a reduced risk of embolic complications when surface eroding polymers are employed, even when used in conjunction with fabric sheaths of very high porosity.

In one preferred embodiment of the invention, as depicted in FIG. 2, the annuloplasty ring may further comprise a flexible, elastomeric-like covering material 22 surrounding the biodegradable ring insert 14, positioned between the ring insert 14 and the fabric sheath 24. For example, the ring insert may be inserted into or otherwise enclosed within a material such as silicone rubber, poly(ether urethane), polytetraflouorethylene, or other like materials. This may be most readily achieved by inserting the biodegradable insert into a length of elastomeric tubing having an appropriate internal diameter similar to or slightly smaller than the diameter of the biodegradable insert. The use of these elastomeric tubing materials in modern annuloplasty rings is well known and therefore not described in further detail herein. Once the biodegradable ring insert is enclosed within this elastomeric covering, the insert and covering are then inserted and sealed within the described fabric sheath prior to use.

As would be apparent to the skilled individual in this art, other materials and/or compounds may be combined before, during, or subsequent to formation of one or more of the components of the present annuloplasty ring, or added to, coated onto, etc, during or after its fabrication. These compounds may include essentially anything which will not unacceptably interfere with the desired properties of the biodegradable insert, e.g., its desired initial rigidity, its biodegradability, and/or its ability to degrade into components that are substantially innocuous to living systems. Examples of such substances may include, without limitation, plasticizers, stabilizers, pigments, dyes, radioopaque materials, lubricants, antioxidants, bioactive agents, antimicrobial agents, and the like.

According to the present invention, at least some portion of the described annuloplasty ring has incorporated therein, adhered thereto, etc., one or more antithrombogenic agents. For example, one or more antithrombogenic agents may be incorporated into the biodegradeable ring insert 14, the elastomeric like covering 22, or, more preferably, the fabric sheath 24 (See FIG. 2). Numerous antithrombogenic treatment processes have been described for causing the incorporation of antithrombogenic and other bioactive agents into or onto a medical device, and the skilled individual would recognize the applicability of such approaches to the present invention.

"Antithrombogenic," as this term is used herein in reference to the medical devices produced according to the present invention, is intended to encompass essentially any medical device which has been treated under conditions effective for incorporating into or onto at least some portion of the device, either directly or indirectly, the desired antithrombogenic agent(s) and/or material(s). As a result, the portion of the device treated by this antithrombogenic treatment process will preferably exhibit some degree of antithrombogenic activity, as determined, for example, by its ability to inhibit thrombin-catalyzed fibrin clot formation, its ability to inhibit the amidolytic activity of thrombin, or by its ability to cause a substantial reduction in other known measures of the thrombogenic response when compared with a medical device that has not been so treated.

Antithrombogenic agents are well known and readily available to the individual skilled in this art. Examples of antithrombogenic or nonthrombogenic agents and materials suitable for use in accordance with this invention may include or be at least partly comprised of heparin, hirudin, albumin, phospholipids, streptokinase, tissue plasminogen activator (TPA), urokinase, hydrophilic polymers such as hyaluronic acid, chitosan, methyl cellulose, poly(ethylene oxide), poly(vinyl pyrrolidone), growth factors such as endothelial cell growth factor, epithelial growth factor, osteoblast growth factor, fibroblast growth factor, platelet derived growth factor (PDGF), and angiogenic growth factor, other like compounds, and functionally equivalent variants and/or derivatives thereof.

The approach by which an antithrombogenic agent is incorporated into or onto some or all of a medical device is not limiting, and may be selected from any of a number of methods available in the art, some illustrative examples of which are described below.

For example, U.S. Pat. No. 5,679,659, assigned to Medtronic Inc., the disclosure of which is incorporated herein by reference, describes a method for making a heparinized medical device. In this method, heparin is reacted with a periodate compound and this mixture is reacted and then applied to immobilized amine groups on a medical device surface. The application to the immobilized amine groups causes a reaction between the aldehyde groups on the heparin and the immobilized amine groups to form a Schiff base. A mild reducing agent is used to stabilize the Schiff base into a secondary amine.

The amine groups may be provided on the medical device surface by methods known to those skilled in the art. For example, amine-functional spacer molecules have been used to immobilize biomolecules. The spacer insures that the active site of the biomolecule is held outward away from the support so as to contact the body fluid efficiently. The spacers are derived from organic molecules having at least two reactive functional groups generally situated at opposing ends of the molecule. Such groups serve as attachment vehicles capable of coupling the spacer to the solid surface and to the biomolecule.

The immobilized amine functionality is generally provided in a manner similar to that disclosed in U.S. Pat. No. 5,308,641 in which a polyalkyeneimine is covalently attached to a substrate. Polyalkyleneimine is intended to include the water soluble, hydrophilic, polyamines evolving from aziridine and azetidine monomers such as 1-unsubstituted imines, 1-substituted basic imines, activated imines (1-acyl substituted imines), isomeric oxazolines/ oxazines and the like. The polyalkyleneimines are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used.

An important aspect of this heparin immobilization process is the controlled oxidation of the heparin molecules to provide a limited number of reactive aldehyde groups on the average heparin molecule. This is accomplished by adding a periodate to a buffered aqueous solution of the heparin and allowing it to react with the heparin. Any water soluble periodate can be used but preferably the periodate is an alkali metal periodate such as sodium periodate. If the periodate used is sodium periodate and the heparin used is a commercially available injectable form of heparin (i.e. its sodium salt with activity of about 160 u/mg), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

In another example of a method for providing an anti-thrombogenic agent on a medical device, U.S. Pat. No. 5,865,814, assigned to Medtronic Inc., the disclosure of which is incorporated herein by reference, describes an approach whereby an aqueous heparin solution is applied to a stent device and the water is allowed to evaporate, thereby leaving on the stent surface a coating of heparin. Typically, the solution can be applied by either spraying the solution onto the device or immersing the device in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the device. In either a coating applied by spraying or by immersion, multiple application steps are generally desirable to provide optimal coating uniformity and improved control over the amount of antithrombogenic agent to be applied to the device.

In order to provide control over the elution of heparin from the device when using this approach, a porous polymeric overlayer may also applied to the device. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response.

With an aqueous coating of heparin is provided on the device, the polymer overlayer is important in controlling the elution from the implanted device since the heparin is water soluble and would otherwise elute immediately without providing a desired long term benefit. For example, an aqueous coating of heparin can be provided by spraying a solution or dispersion of heparin onto the device body. When the applied heparin layer is dry, a solution of chloroform and poly(L-lactic acid) could be used to form the overlayer by spraying the polymer solution onto the device as disclosed above.

The overlayer is preferably provided in porous form. A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-lactic acid) as the polymer, a suitable solvent composition can include about a 40/60% (w/w) isooctane/chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly (L-lactic acid) solution). This mixture is then applied to the device. It will be appreciated by those skilled in the art that the nature of the ingredients and the relative concentrations of the ingredients will determine the size of pores.

Other methods for providing antithrombogenic surfaces, for example as described in U.S. Pat. Nos. 5,512,329 and 5,741,551, the disclosures of which are incorporated herein by reference, and other related patents assigned to BSI Corporation, relate to methods for modifying substrate surfaces by bonding molecules, e.g., protein molecules, to substrates through external activation of latent reactive groups carried on the molecules. The latent reactive groups are groups which respond to specific applied external stimuli to undergo active specie generation with resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups are generally well known and may be chosen to be responsive to various portions of the electromagnetic spectrum.

Utilizing reactive chemical units bearing latent reactive groups, one will desirably first coat a surface or other substrate with a solvent solution of such molecules. Upon removal of solvent, the application of an appropriate external stimulus such as U.V. light will cause the molecules to covalently bond, through the latent reactive groups, to the substrate. The substrate may then be appropriately contacted with a solution containing the desired polymer, monomer or oligomer molecules to cause bonding to these molecules.

The loading density resulting from attachment of polymer molecules to a surface or other substrate in accordance with the above method may be regulated in several ways. First, the degree of activation of latent reactive groups is generally a function of the quantity of the external stimulus that is applied, and thus the extent of covalent bonding through the latent reactive groups may be regulated by regulating the intensity and time of application of the applied stimulus. Regulation of the applied stimulus is particularly easy when the stimulus is actinic radiation; one can readily regulate the amount of radiation to which the latent reactive groups are exposed. Loading density may also be regulated by adjusting the capacity of polymer molecules of the invention to bring their latent reactive groups into bonding proximity with a surface. Thus, one may regulate the viscosity of a solution of polymer molecules in an appropriate solvent as well as the solubility of polymer in the solvent.

Hirudin, a naturally occurring anticoagulant, has also been used to provide antithrombogenic surfaces. For example, European Patent Application No. 0 200 655 describes a method for treating materials for use in medical devices in which the surface is treated with a wetting solution of a paladium or rhodium salt and then treated with an anticoagulant such as heparin or hirudin under conditions to produce ionically bound coatings.

In addition, U.S. Pat. No. , 5,053,453, assigned to Baxter Inc., the disclosure of which is incorporated herein by reference, describes coupling hirudin or hirudin derivatives either directly to the functional groups of a support material or by way of linking groups. The method generally comprises coupling the hirudin or hirudin derivative by a functional group of an amino acid residue to an active functional group of a substrate support material. The method for coupling is dependent upon several factors including the available functional groups on the support material, the coupling site or sites on the protein, biological activity of the resulting material, selectivity and efficiency of the coupling reaction.

For example, if the coupling sight on the protein, i.e. the amino acid residue, is not in close proximity to the active sight of the protein, i.e. the thrombin binding region, and the support material contains the appropriate active functional groups, the protein may be directly coupled to the support material utilizing reactions known to those skilled in the art. Alternatively, the protein can be coupled to the support material by a linking group. Examples of linking groups include, bifunctional reagents such as bifunctional protein crosslinking reagents, polypeptides, proteins, protein segments, and multifunctional polymers such as polyethyleneimines or dendritic polymers. The choice of a linking group can depend on the coupling site, the functional groups of the support material, biological activity of the resulting material and the efficiency and selectivity of the coupling reaction. For example, the phenolic group of tyrosine can be modified using bifunctional reagents such as N-(4-diazobenzoyl)-N(3-maleimidopropionyl)hydrazine-tetrafluoroborate (DMHT) and N-succinimidyl-3-(2-pyridyldithio) propionate (SPDP) to add a sulfhydryl group for coupling with support materials which have active amino groups.

Conjugates of hirudin and support materials can be made according to this method using a variety of bifunctional protein crosslinking reagents. Examples of such reagents include SPDP, bifunctional derivatives of imidoesters such as dimethyl adipimidate and dimethyl suberimidate, active esters such as disuccinimidyl suberate, aldehydes such as glutaraldehyde and glycolaldehyde, bis-azido compounds such as bis-(p-azidobenzoyl) hexanediamine, bis-diazonium derivatives such as bis-(p-diazoniumbenzoyl)-ethylenediamine, diisocyanates such as tolylene-2,6-diisocyanate and tolylene-2,4-diisocyanate, and bis-active fluorine compounds such as 1,5-difluoro-2,4-dinitrobenzene and other reagents such as ethylene glycol/bis[succinimidyl succinate], m-maleimido benzoyl sulfasuccinimide, and diethylene triamine pentacetic acid anhydride.

Where the biological activity of the protein would be greatly reduced by direct coupling due to steric hindrance, such as coupling at the C-terminal residue, or sticking of the protein to the support material, it can be desirable to use a linking group which would act to space the protein away from the support material. Examples of such linking groups include, but are not limited to, polypeptides, proteins and multifunctional polymers. Such linking groups can also provide multiple sites for attachment of the hirudin or hirudin derivatives to increase the binding efficiency.

In addition to the examples described above, many other antithrombogenic treatment methods are similarly known and available to the skilled individual in the art for use in conjunction with the medical devices of this invention, including, but not limited to, methods for providing substrate surfaces with agents such as heparin, e.g., U.S. Pat. Nos. 3,511,684, 3,585,647, 4,254,180, 4,331,697, 4,676,974, 4,526,714, 4,634,762, 4,678,660, 4,678,671 and 5,877,263, phospholipids, e.g., U.S. Pat. No. 5,556,632, chitosan, e.g., U.S. Pat. No. 4,326,532, antithrombogenic polymers, e.g., U.S. Pat. Nos. 4,521,564, 4,600,652 and 4,642,242, and others, e.g., U.S. Pat. Nos. 4,973,493, 4,979,959, 5,263,992, 5,414,075, 5,512,329 and 5,741,551, the disclosures of which are incorporated herein by reference.

The above approaches for incorporating antithrombogenic agents or materials into or onto substrate surfaces are described for illustrative purposes only. As will be apparent to the skilled individual, the particular method employed for providing an antithromobogenic medical device for use in this invention may be selected from any of a variety of conventional approaches. Of course, it will generally be desired that the antithrombogenic treatment process is selected and performed such that the process and resulting surface-modified product is compatible with and does not adversely effect any prior, subsequent or simultaneously performed treatment processes according to this invention.

The phrases "incorporation into" and "incorporating into," as used herein, means that at least some antithrombogenic agent permeates, adheres to, or otherwise becomes associated with one or more of the polymeric structures of which the annuloplasty ring is comprised, e.g., the ring insert, the elastomeric-like covering and/or the outer fabric sheath. Thus, the antithrombogenic agent may be largely associated with the surface of the device, as in a coating, may penetrate within or between the polymeric structure that makes up the device, may be covalently or ionically bound to the device structure, etc. The nature of the association between the antithrombogenic agent and the annuloplasty ring may depend on the particular agent used, the antithrombogenic treatment processes employed, and/or the type and structure of the component or components of the annuloplasty ring being treated.

The extent of incorporation of the antithrombogenic agents or materials into or onto the annuloplasty ring may be evaluated by any of a number of approaches. For example, the incorporation may be assessed by mass analysis of the device before and after treatment. Alternatively, the incorporated agent may be extracted or otherwise removed from the device using an appropriate method and analyzed by a suitable quantitative technique, e.g., high-performance liquid chromatography or ultraviolet/visible spectroscopy. The extent and effectiveness of incorporation may also be evaluated by more functional approaches, i.e., wherein antithrombogenic activities are assayed by suitable in vitro or in vivo testing apparent to the skilled individual.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An annuloplasty ring comprising:
   a ring insert at least partly comprised of a surface eroding biodegradable polymer material group consisting of polyanhydrides, polyvinylpyrolidone, and polyvinyl alcohol;
   an elastomeric sheath enclosing said ring insert;
   a fabric sheath enclosing said ring insert and said elastomeric sheath; and
   one or more antithrombogenic agents or materials incorporated into at least some portion of the annuloplasty ring.

2. The annuloplasty ring of claim 1, wherein the antithrombogenic agents or materials are at least partly comprised of heparin, hirudin, albumin, phospholipids, streptokinase, tissue plasminogen activator (TPA), urokinase, hyaluronic acid, chitosan, methyl cellulose, poly (ethylene oxide), poly(vinyl pyrrolidone), endothclial cell growth factor, epithelial growth factor, osteoblast growth factor, fibroblast growth factor, platelet derived growth factor or angiogenic growth factor.

3. The annuloplasty ring of claim 1, wherein the antithrombogenic agents or materials are covalently or ionically incorporated into the annuloplasty ring.

4. The annuloplasty ring of claim 1, wherein the antithrombogenic agents or materials are ionically or covalently incorporated into the fabric sheath of the annuloplasty ring.

5. The annuloplasty ring of claim 1, wherein the surface eroding biodegradable polymer material comprises a photopolymerizable polyanhydride.

6. The annuloplasty ring of claim 1, wherein the surface eroding biodegradable polymer material comprises a polyanhydride polymerized from methacrylate anhydride monomers.

7. The annuloplasty ring of claim 6, wherein the methacrylate anhydride monomers are synthesized from diacid molecules of sebacic acid or 1,6-bis(p-carboxyphenoxy)-hexane.

8. The annuloplasty ring of claim 6, wherein the surface eroding biodegradable polymer material comprises a a copolymer of methacrylate anhydride monomers synthesized from diacid molecules of sebacic acid and 1,6-bis(pcarboxyphenoxy)-hexane.

9. The annuloplasty ring of claim 1, wherein the fabric sheath is comprised of a polymeric material.

10. The annuloplasty ring of claim 1, wherein the fabric sheath is comprised of a polymeric material selected from the group consisting of polyethyleneterephthalate, polytetrafluoroethylene and polyester (polyacetate).

11. The annuloplasty ring of claim 1, wherein the elastomeric sheath is comprised of a silicone rubber, a poly(ether urethane) or a polytetrafluoroethylene.

12. The annuloplasty ring of claim 1, wherein the ring insert further comprises one or more plasticizers, stabilizers, pigments, dyes, radio-opaque materials, lubricants, antioxidants, bioactive agents or antimicrobial agents.

13. A method for making an annuloplasty ring comprising:
   forming a ring insert at least partly comprised of a surface eroding biodegradable polymer material from the group consisting of polyanhydrides, polyvinylpyrrolidone, and polyvinyl alcohol;
   enclosing at least a portion of said ring insert in an elastomeric sheath;
   enclosing at least a portion of said ring insert and said elastomeric sheath in a fabric sheath; and
   incorporating one or more antithrombogenic agents or materials into at least some portion of the annuloplasty ring.

14. The method of claim 13, wherein the antithrombogenic agents or materials are at least partly comprised of heparin, hirudin, albumin, phospholipids, streptokinase, tissue plasminogen activator (TPA), urokinase, hyaluronic acid, chitosan, methyl cellulose, poly(ethylene oxide), poly(vinyl pyrrolidone), endothclial cell growth factor, epithelial growth factor, osteoblast growth factor, fibroblast growth factor, platelet derived growth factor or angiogenic growth factor.

15. The method of claim 13, wherein the antithrombogenic agents or materials are covalently or ionically incorporated into with the annuloplasty ring.

16. The method of claim 13, wherein the antithrombogenic agents or materials are ionically or covalently incorporated into the fabric sheath of the annuloplasty ring.

17. The method of claim 13, wherein the ring insert is formed by molding, extrusion or machining the surface eroding biodegradable polymer material.

18. The method of claim 13, wherein the surface eroding biodegradable polymer material comprises a photopolymerizable polyanhydride.

19. The method of claim 13, wherein the surface eroding biodegradable polymer material comprises a polyanhydride polymerized from methacrylate anhydride monomers.

20. The method of claim 19, wherein the methacrylate anhydride monomers are synthesized from diacid molecules of sebacic acid or 1,6-bis(p-carboxyphenoxy)-hexane.

21. The method of claim 19, wherein the surface eroding biodegradable polymer material comprises a copolymer of methacrylate anhydride monomers synthesized from diacid molecules of sebacic acid and 1,6-bis(p-carboxyphenoxy)-hexane.

22. The method of claim 13, wherein said fabric sheath is comprised of a polymeric material.

23. The method of claim 22, wherein said fabric sheath comprises a polymeric material selected from the group consisting of polyethyleneterephthalate, polytetrafluoroethylene and polyester (polyacetate).

24. The method of claim 13, wherein the elastomeric sheath is comprised of a silicone rubber, a poly(ether urethane) or a polyetrafluoroethylene.

25. The method of claim 13, wherein the ring insert further comprises one or more plasticizers, stabilizers, pigments, dyes, radioopaque materials, lubricants, antioxidants, bioactive agents or antimicrobial agents.

* * * * *